United States Patent [19]
Bonne et al.

[11] Patent Number: 5,533,393
[45] Date of Patent: Jul. 9, 1996

[54] DETERMINATION OF DEW POINT OR ABSOLUTE HUMIDITY

[75] Inventors: Ulrich Bonne, Hopkins, Minn.; Nobuaki Honda, Yokohama, Japan; David Kubisiak, Chanhassen; Thomas R. Ohnstein, Roseville, both of Minn.

[73] Assignee: Honeywell Inc., Minneapolis, Minn.

[21] Appl. No.: 372,577

[22] Filed: Jan. 13, 1995

[51] Int. Cl.⁶ ............ G01N 27/12; G01W 1/00; H01L 7/00
[52] U.S. Cl. .......... 73/355.02; 73/29.01; 73/29.02; 73/335.05; 338/34; 374/28; 324/663; 324/689; 340/602; 340/580
[58] Field of Search .............. 73/335.02, 336.50, 73/29.01, 29.02; 338/34, 35; 374/28; 324/663, 689, 694; 340/602, 580

[56] References Cited

U.S. PATENT DOCUMENTS

| | | | |
|---|---|---|---|
| 3,075,385 | 1/1963 | Stover | 73/335 |
| 3,175,400 | 3/1965 | Amdur | 73/336.5 |
| 3,265,301 | 8/1966 | Amdur et al. | 236/44 |
| 3,664,192 | 5/1972 | Campbell et al. | 73/336.5 |
| 3,689,907 | 9/1972 | Guajardo | 340/235 |
| 3,703,696 | 11/1972 | Browall et al. | 338/35 |
| 4,167,725 | 9/1979 | Shimizu et al. | 338/35 |
| 4,203,087 | 5/1980 | Kovac | 338/35 |
| 4,373,339 | 2/1983 | Johnson | 73/335 |
| 4,378,168 | 3/1983 | Kuisma et al. | 374/28 |
| 4,379,406 | 4/1983 | Bennewitz | 73/336.5 |
| 4,441,968 | 4/1984 | Emmers | 204/35 N |
| 4,442,422 | 4/1984 | Murata et al. | 338/35 |
| 4,482,581 | 11/1984 | Lorin et al. | 427/79 |
| 4,621,249 | 11/1986 | Uchikawa et al. | 338/34 |
| 4,632,879 | 12/1986 | Tanaka et al. | 428/522 |
| 4,638,346 | 1/1987 | Inami et al. | 357/25 |
| 4,642,601 | 2/1987 | Sugawara et al. | 338/35 |
| 4,651,121 | 3/1987 | Furabayashi et al. | 338/35 |
| 4,696,796 | 9/1987 | Oka | 422/88 |
| 4,703,555 | 11/1987 | Hübner | 29/611 |
| 4,723,439 | 2/1988 | Asakura | 73/29 |
| 4,760,368 | 7/1988 | Sugihara et al. | 338/34 |
| 4,761,710 | 8/1988 | Chen | 361/286 |
| 4,784,721 | 11/1988 | Holmen et al. | 156/647 |
| 4,793,181 | 12/1988 | Djorup | 73/336.5 |
| 4,793,182 | 12/1988 | Djorup | 73/336.5 |
| 4,805,070 | 2/1989 | Koontz et al. | 361/286 |
| 4,920,451 | 4/1990 | Sakai et al. | 361/286 |
| 4,928,513 | 5/1990 | Sugihara et al. | 73/1 G |
| 4,948,263 | 8/1990 | Herrmann et al. | 374/28 |
| 5,036,704 | 8/1991 | Pusatcioglu | 73/336.5 |
| 5,317,274 | 5/1994 | Nakagawa | 324/678 |

OTHER PUBLICATIONS

Chapter 37, "Polycarboxylic Acids", *Chemistry of Organic Compounds*, pp. 791–792.
Lambert, David K. et al, "An air flow sensor based on interface thermal wage propagation", J. Appl. Phys., 59(1) Jan. 1986, pp. 59–65.

*Primary Examiner*—Hezron E. Williams
*Assistant Examiner*—J. David Wiggins
*Attorney, Agent, or Firm*—Haugen and Nikolai

[57] ABSTRACT

A microsensor system for determining water vapor content of the ambient atmosphere that uses a thin film suspended ceramic diaphragm structure featuring an embedded, patterned thin film heater, temperature sensor and an external film of an hygroscopic salt stabilized in a water-insoluble, crosslinked polymer matrix and contacting a pair of patterned electrodes which are proximate to the heater. The heater controls a selected electrical parameter of the salt to a fixed, predetermined value, as determined by its electrical characteristics. The dew point of the atmosphere is determined based on the dynamic relation with the salt dehydration temperature.

37 Claims, 4 Drawing Sheets

DETERMINATION OF DEW POINT OR ABSOLUTE HUMIDITY

BACKGROUND OF THE INVENTION

I. Field of the Invention

The present invention relates generally to dew point or humidity sensing and, more particularly, to dew point sensing using hydrophilic alkali metal salts in a heated equilibrium mode. The invention provides an improved, inexpensive, miniaturized, quick-response, dew point or humidity sensor characterized by long-term salt stability and low power consumption.

II. Related Art

The water absorption properties of a number of hygroscopic materials including alkali metal halide salts are known and have been employed as detection mechanisms for sensing dew point for many years. Thus, it is known that changes in water content or degree of water saturation in the salt changes the conductivity of the material which can be sensed between adjacent electrodes as a function of relative humidity. This approach has been implemented mainly using lithium chloride (LiCl) as the hygroscopic material. Commercial bulk-type dew point sensors have been fabricated with LiCl and, while functional, these sensors have had several undesirable characteristics. They generally have been relatively large and bulky leading to a correspondingly undesirably slow response time. Those heated directly have needed an applied voltage level that is well above the electrochemical potential of the electrolyte/metal system, which led to poor stability and to shorter service life.

The principle that an hygroscopic salt exposed to ambient atmosphere and supplied with a regulated heat input can be caused to maintain a substantially constant predetermined resistance at equilibrium by absorbing and releasing moisture to the ambient atmosphere is known. It is further known that the temperature required to maintain this condition of equilibrium between the salt and the atmosphere that produces a given resistance is related to the dew point of the ambient atmosphere in a direct manner such that as the dew point or moisture content of the ambient atmosphere rises, the required equilibrium temperature likewise increases. In fact, it has further been found that the temperature to which the salt must be heated to maintain resistivity of the salt at its preselected level is, within narrow uncertainty limits, directly proportional to the water vapor content of the atmosphere.

Dew point measuring devices have been manufactured pursuant to this principle and in one such device a thermistor, or the like, embedded within the sensor unit of the hygrometer is utilized to produce a temperature signal that is in direct relation to the dew point of the atmosphere and, in this manner, the dew point is determined. Such a device is illustrated and described in U.S. Pat. No. 3,664,192. While this device has met with some success, there remains a definite need for a microminiaturized highly accurate dew point sensor which responds rapidly to changes in dew point, in which the hygroscopic salt is stabilized against washout and which can operate on low LiCl-electrode voltage and power input to achieve the desired service life.

Accordingly, it is an object of the invention to provide a low cost, microminiaturized dew point or humidity sensor characterized by a rapid response time, low power requirement and long life.

Another object of the invention is to provide a LiCl dew point or humidity sensor design that eliminates the problems of washout of the hygroscopic salt at high humidity, electrochemical degradation, and temperature measurement.

A still further object of the invention is to provide a LiCl dew point or humidity sensing device wherein retention of LiCl is accomplished by crosslinking polyvinyl alcohol.

A yet still further object of the invention is to provide a LiCl dew point or humidity sensing device which utilizes an etched diaphragm microsensor.

SUMMARY OF THE INVENTION

In accordance with the invention, an inexpensive, highly sensitive alkali metal salt humidity and dew point sensor has been developed that is extremely small and further exhibits rapid response and long-term stability. The invention includes improvements in using a water insoluble polymer matrix for retaining the alkali metal salt in the sensor and accomplishes great reductions in power consumption owing to its miniaturization.

The preferred sensor is characterized by an anisotropically etched suspended ceramic structure in the form of a microdiaphragm, bridge or cantilever structure. Such a diaphragm is typically less than 2×2 mm in size and less than 10 microns thick, thereby enabling a rapid response to changes in temperature and humidity and the required voltage input is well below a level necessary to effect chemical changes in the alkali metal salt, preferably LiCl. The preferred embodiment undercuts and suspends a silicon nitride $Si_3N_4$ diaphragm carrying a serpentine platinum heater and a temperature sensor, preferably interserpentined with the heater, embedded therein. An interdigital Au/Ag electrode system is patterned on the upper (outer) surface and connected by a LiCl salt layer further contained in a water insoluble polymer retention matrix. The preferred polymer retention matrix is polyvinyl alcohol (PVA) crosslinked by an amount of carboxylic acid, preferably malonic acid (a saturated dicarboxylic acid). UV radiation and a baking step are normally employed to produce the desired retention properties and viscosity for patterning on the sensor surface by screen printing or the like.

The alkali halide element of the sensor is connected in the system as part of one leg of a Wheatstone bridge which is balanced or nulled at a desired or control resistance, which corresponds to a low equilibrium relative humidity, preferably chosen at about ≤10% RH (at normal ambient). The resistance varies greatly with humidity and creates an imbalance in the bridge signal. The amplified imbalance in the Wheatstone bridge ultimately powers the platinum heater as indicated to restore equilibrium above the original null temperature, the null temperature being indicative of the dew point. It is understood that either the resistive or the capacitive imbalance component can be used with an AC input (typically in the range of 100 Hz–1 Mhz) to the Wheatstone bridge, but resistance is described in the detailed embodiment. A time delay or other suitable control is built into the system to obviate a characteristic dip in initial response to temperature step change.

BRIEF DESCRIPTION OF THE DRAWINGS

In the drawings, wherein like numerals designate like parts throughout the same.

DETAILED DESCRIPTION

Figure 1:
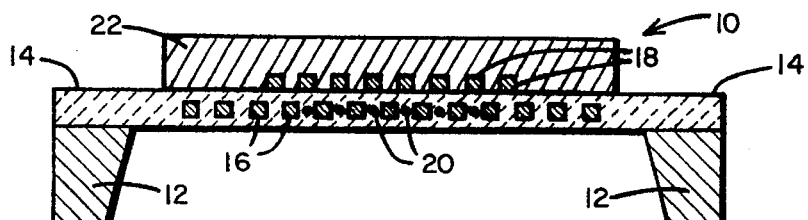
FIG. 1 is a schematic cross-sectional view through a dew point/RH sensor fabricated in accordance with the invention.

FIG. 1 depicts a schematic cross-sectional view through a typical microsensor, generally at 10, fabricated for the humidity/dew point sensing system of the present invention. The entire microsensor may be contained on a substrate that is less than 2×2 mm in surface area and in the form of a suspended bridge, diaphragm or cantilever structure. The structure is typically produced from a body of material, preferably silicon, having a predetermined crystalline structure orientation to which a layer of the material designed to form a suspended structure has been applied as an overlayer on the material surface. At least one predetermined area of the first surface is exposed which is bounded by the predetermined configuration to be suspended and which, in turn, is oriented so that the undercutting thereby by an anisotropic etch will create the desired diaphragm structure. As indicated, such a configuration can be made extremely small and so the sensor pictured in FIG. 1 is shown greatly magnified. Structures of the class are shown, for example, in U.S. Pat. No. 4,784,721 (Holmen et al), assigned to the same assignee as the present application. Greatly enlarged plan views are also depicted in FIGS. 6 and 7.

The body or sensor base portion 12, preferably silicon, the greater portion of which is etched away defining and forming a diaphragm structure with a thin overlayer 14 of self-supporting ceramic material, preferably silicon nitride ($Si_3N_4$) which is typically about 0.8 to 1.4 microns thick for a 1×1 mm diaphragm of the sensor. Sectioned segments of a serpentine style resistance heater, preferably of platinum, are shogun at 16 contained in the layer 14 and a sectioned interdigital electrode configuration is further shown at 18. A temperature sensor 20, also typically arranged in serpentine fashion, is shown interspersed in the central portion of the serpentine heater segment 16. The temperature sensor is preferably limited to the central region of the heated area as this is the most even or constant temperature region. Of course, however, the temperature sensed should be representative of the temperature of the interdigital electrical area including the salt (below). The interdigital electrode pattern is, in turn, embedded in a layer of environmentally-stabilized alkali metal chloride 22, preferably lithium chloride (LiCl). The patterning of the interdigital configuration or pattern 18 and serpentine arrangement 16 are accomplished by well-known thin-film or thick-film patterning techniques, CVD or plasma etching techniques, any of which will occur to those skilled in the art and which need not be detailed further herein.

Figure 6:
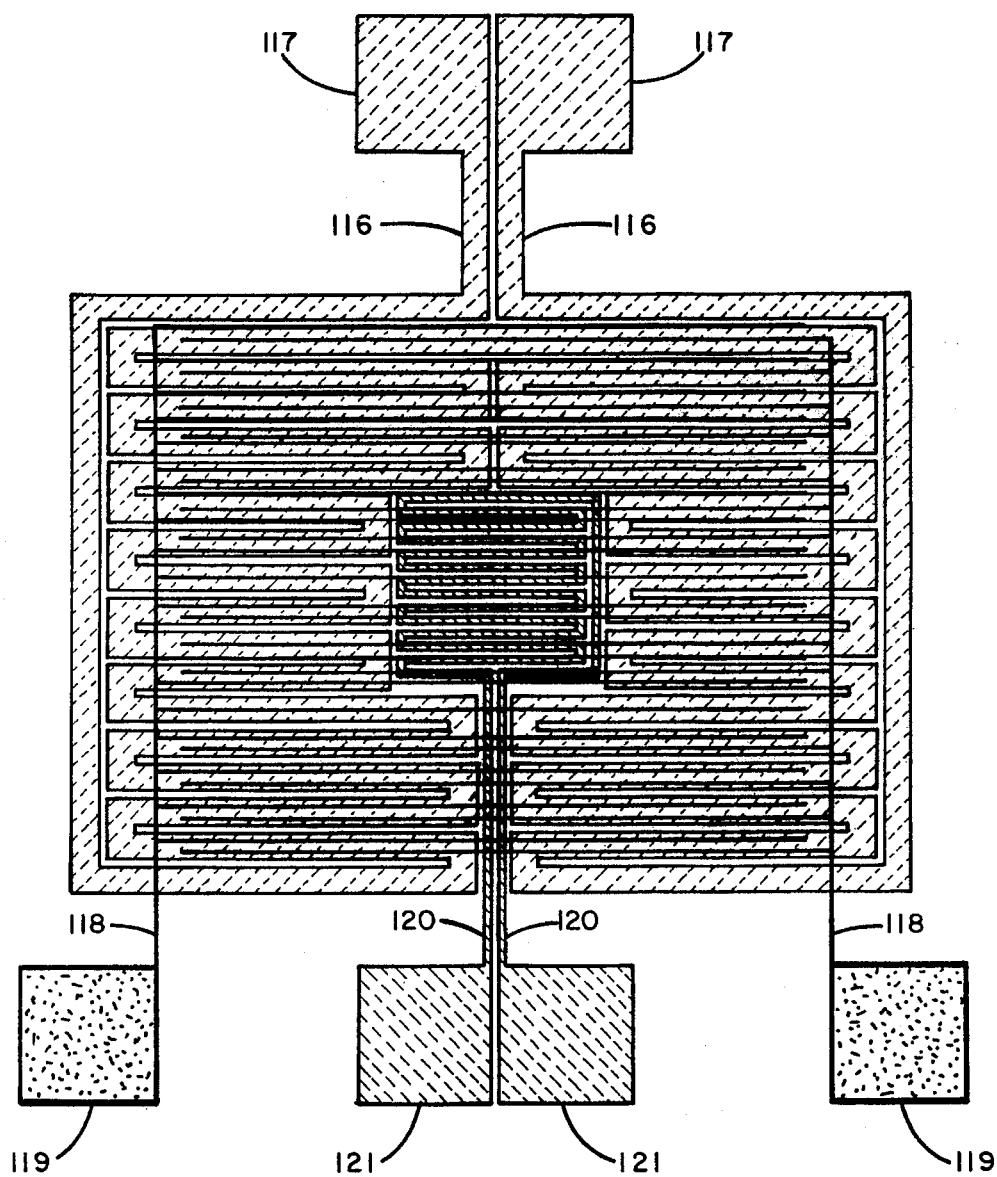
FIG. 6 is a greatly enlarged plan view of one embodiment of a dew point sensor element fabricated in accordance with the invention.

FIG. 6 depicts a greatly enlarged top schematic view of a dew point sensor element fabricated in accordance with the present invention and further illustrating the intricate interrelation of the elements. The schematic of FIG. 6 includes a serpentine-style heater arrangement depicted at 116 which is connected to the circuitry of the system as by connectors 117. The temperature sensor is centrally situated and represented by the serpentine pattern of members 120 with suitable interfacing connectors depicted by 121. The interdigital electrode configuration includes oppositely disposed interdigital or meshing portions 118, each associated with an electrical connector 119. The heater, temperature sensor and electrode elements are typically platinum films which may be applied utilizing any applicable well-known patterning technique. The arrangement of FIG. 6, while sufficient for many purposes, does not compensate variances in the temperature profile generated by the heater across the device and so depends on the use of an averaged LiCl temperature rather than the integration of an accurate profile.

Figure 7:
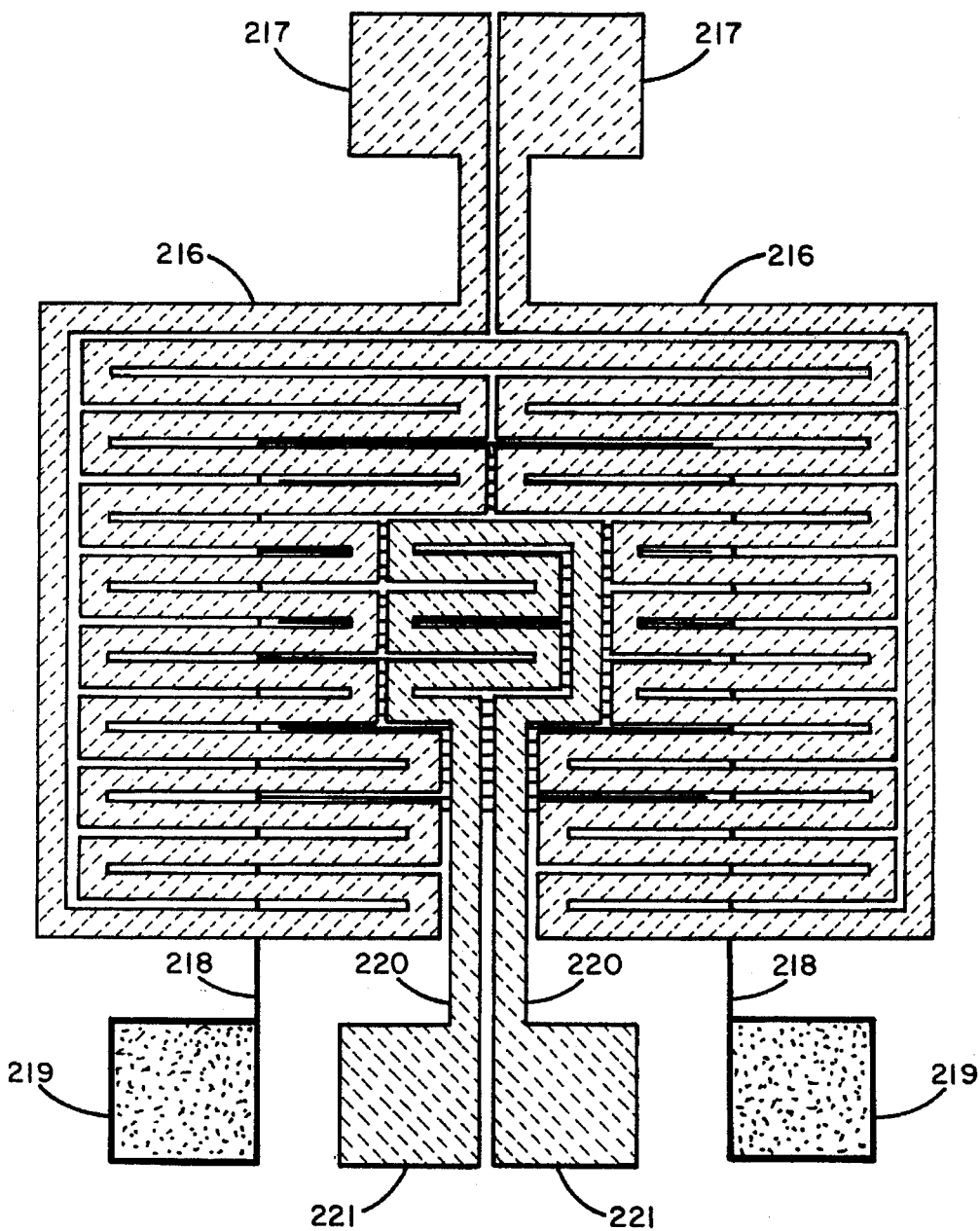
FIG. 7 is a greatly enlarged plan view of another embodiment of the dew point microsensor of the invention showing the central split of the heater used as a temperature sensor.

A possibly somewhat more accurate embodiment is shown in the generally similar, greatly enlarged plan view in the schematic diagram of FIG. 7. Thus, a serpentine resistance heater is depicted by 216 with terminals 217. An interdigital electrode system including interdigital pattern portions 218 with connectors or leads 219 is shown occupying a relatively smaller central section of the portion covered by the serpentine heater 216. The temperature sensor 220 is further shown in the central part of a serpentine resistance heater arrangement with leads 221. By limiting the LiCl conductivity sensing electrodes to a more limited central area surrounding the temperature sensing area, the inconsistencies produced by the existence of an overall temperature profile, which is not flat, are reduced. The temperature sensor 220 also doubles as part of the heater system in this arrangement and is operated by the same or possibly slightly lower current than the heater 216 has been found to provide sufficient resistance to allow accurate resistance measurement and thus accurate temperature determination with respect to the temperature of the LiCl salt in the central area.

Of course, the serpentine heater 16, 116, 216 can be made to cover the entire area and the temperature sensor system made to be superimposed with respect to the heater. This version may be preferred for certain applications.

According to an important aspect of the invention, the representative salt, preferably LiCl, is retained in a manner that allows rapid free exchange of water vapor with the ambient environment without loss of LiCl even at saturated or high relative humidity (RH) conditions. The retention mechanism of the invention enables the LiCl to sustain a temperature of about 130° C. and remain intact. In accordance with the preferred embodiment, superior retention against washout is achieved without impairing sensitivity.

In regard to the stabilized retention of the salt in contact with the electrodes, several systems have been employed with varying degrees of success. Polyethylene oxide (PEO) has been examined as the host material to retain LiCl. PEO has strong absorption properties; however, PEO is water soluble and cannot prevent LiCl washout under conditions of saturation and high humidity. Polyacrylonitrile (PAN) includes the functional group (—CN), the premise being that LiCl be retained by hydrogen bonding force of the functional group with the dipole moment of the polymer. However, it has been found that PAN alone cannot retain salts such as LiCl well enough to prevent washout when they absorb large amounts of water. A combination of PEO and PAN improves high humidity retention properties for PAN and may be useful but a more hydrophilic material is preferred.

According to the invention, the preferred material for retaining the salt material is a water-stabilized or crosslinked poly alcohol of which the preferred material is polyvinyl alcohol (PVA). PVA material (weight average molecular weight, $M_w$, (in the soluble range of about 25,000–100,000) is hydrophilic and, like LiCl, soluble in water such that a solution including LiCl and PVA can be achieved which, when coated on a surface, such as that of the sensor of the invention, has a large conductance change near the phase transition point of the LiCl. Such a phenomenon has been found to occur at a weight ratio of PVA to LiCl of approximately 1:1. Films of 1:1 PVA LiCl solution spin-coated on wafers and tested in high humidity show that the LiCl absorbs sufficient water to dissolve the PVA film in a LiCl solution. In accordance with the invention, however, prevention of this latter phenomenon has been accomplished by rendering the PVA film insoluble in the LiCl solution without loss of useful LiCl temperature range and sensitivity. This has been accomplished by crosslinking the PVA polymer in a manner that makes the polymer molecular weight larger such that the polymer becomes insoluble or difficult to dissolve in water.

According to the present invention, the preferred crosslinking method uses a saturated carboxylic acid as a crosslinking agent making the PVA UV sensitive, and this together with a baking process has produced excellent crosslinking. The preferred crosslinking agent is malonic acid $CH_2(COOH)_2$. According to the invention, it has been found that exposing a PVA/LiCl system including an adequate amount of $CH_2(COOH)_2$ and exposing it to incident UV for from five to sixty minutes followed by baking at 100° C. to 130° C. for thirty seconds to five minutes produces good results. In this regard, the preferred PVA has a molecular weight from about 49,000 to about 100,000 and the amount of malonic acid should be kept to a minimum inasmuch as the malonic acid does somewhat reduce the conductance change of the PVA/LiCl system which produces a negative effect on the resolution of the dew point sensor. The molecular weight of the PVA and the relative amount of crosslinking agent can be adjusted to produce the desired combination of insolubility and viscosity. The preferred weight ratio of PVA to malonic acid is from about 1.0: 0.1 to 1.0: 0.4 with the most preferred ratio occurring at 1.0: 0.24.

Any conventional method can be utilized to coat the PVA/LiCl polymer solution on the microsensor including PVA photolithography, patterning by dry etching, lift-off and spraying utilizing a mask. Polymer patterning has even been accomplished by the use of a patterned silicone stamp technique.

The presently preferred method for patterning the polymer, however, has been screen printing. This has been accomplished using a number 200 mesh screen. Utilizing this method, the viscosity of the PVA solution is adjusted such that penetration of the screen mesh that is just sufficient to accomplish the desired patterning occurs. Whereas no method can be described as ideal, the screen printing method has given the best results to date with respect to uniformity of thickness and alignment and patterning accuracy.

It is further anticipated that a porous silicon film or a film selected from alumina, magnesia or zirconia may be employed as the host material for LiCl as well. These materials avoid the difficulties associated with polymer host material and polymer patterning. Use of a porous host selected from silicon, alumina, magnesia or zirconia would allow operation at much higher temperatures than PVA (at least 200° C.).

Figure 3:
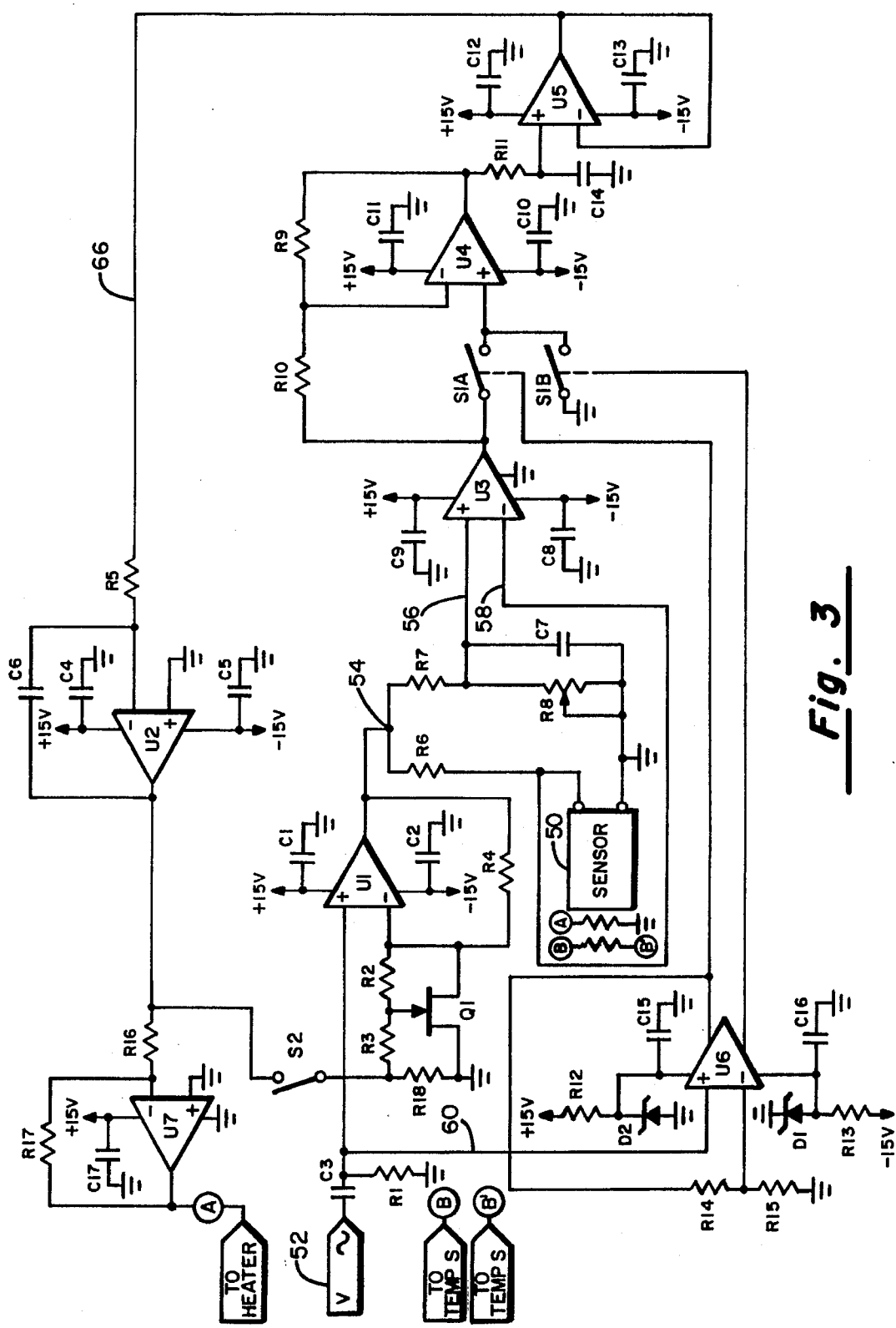
FIG. 3 is a schematic diagram of an embodiment of an operating circuit for the dew point/RH sensor of FIG. 1.

Measurement of the dew point by using two LiCl cell impedance measurements at different frequencies is also contemplated by the invention inasmuch as that measurement technique possibly could be more accurate than the single frequency impedance measurement approach. The ratio of those two signals can be advantageously used to represent cell moisture content with greater consistency, although the electronics is more complex. The measurement method using two different frequencies avoids possible inaccuracies introduced by "drifting" of the sensor because it uses the ratio of the electrical parameter. The circuit of FIG. 3 was designed to operate at one frequency but may be adapted by those skilled in the art to allow the use of two frequencies. The use of a measurement method involving the ratio of impedances obtained at two different frequencies characteristically overcomes difficulties associated with tying the measurement to any absolute value of conductance or impedance with respect to dew point sensor operation.

The preferred material for the interdigital electrodes 18 is a gold/silver alloy, Au 75%/Ag 25% alloy conductor being preferred. This replaces the platinum electrode material typically used inasmuch as Au/Ag alloy is a better electrode material for LiCl conductivity cells in which platinum has been known to be unstable. The Au and Ag can be deposited alternately using a co-sputtering method which involves two targets (Au & Ag) simultaneously addressed by target power splitting. Thus, as the substrate holder is rotated, the Au and Ag are deposited alternately when the substrate passes under each target. The interdiffusion by annealing can be used to achieve uniform concentration of Au and Ag. Annealing conditions achieved by heating to 450° C. for two hours in forming gas (nitrogen and hydrogen) were used.

The Au/Ag alloy electrodes can be patterned by wet etching; however, ion milling is much preferred as wet etching produces too much undercutting of the Au/Ag thin-film layer. This typically achieves a 0.3 micron resolution.

The preferred system for the serpentine heater arrangement consists of an annealed platinum film patterned also by ion milling. Typically achieving a 3 micron line and space configuration.

Figure 2:
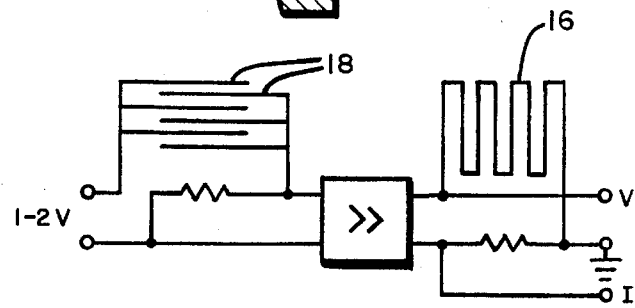
FIG. 2 is a schematic diagram of the electrode pattern and resistance heater system of the sensor of FIG. 1.

A simplified schematic diagram of the sensor system of the invention appears in FIG. 2 including the preferably platinum heater 16 and interdigital electrode system 18. The system operates and will be described in accordance with the more detailed schematic diagram of FIG. 3 in which the electrolytic sensing element 50 of the sensor of the invention is incorporated in one leg of a Wheatstone bridge along with resistive legs R6 and R7 together with variable resistive leg R8 which, with capacitor C7, provides a mode of nulling (balancing) or calibrating the zero point of the sensing element 50 to the lowest relative humidity (RH) value that still offers a reliable and repeatable conductivity. In this way, the temperature of the sensing element is controlled to maintain its conductivity or impedance constant at all times. Furthermore, this circuit uses a separate temperature sensor in order to achieve a more reliable measurement.

A sinusoidal voltage input (typically 1K to 10K Hz) received at 52 is capacitively coupled at C3. The sine wave is amplified at U1 and the output is applied to the Wheatstone bridge at 54. Variable resistor R8 with parallel capacitor C7 are provided to enable the bridge to be balanced or zeroed in accordance with the desired zero point at the lowest RH value. The output of both sides of the Wheatstone bridge on lines 56 and 58 is provided as the input to differential amplifier U3. This amplifies any Wheatstone bridge differential or imbalance between the signal on lines 56 and 58, which corresponds to the sensor signal, thereby amplifying the sensor signal for further processing. The gain of U3 is typically about 100 making the sensor signal easier to process further.

The output of U3 is fed through a synchronous demodulator system which includes switches SIA and SIB and amplifiers U4 and U5. Synchronization or timing of the system is provided by the incoming voltage sine wave on line 60 as further processed by a comparator U6 which converts the incoming sinusoidal voltage into a pair of outputs on lines 62 and 64 in the form of two square wave logic signals which are 180° out of phase with each other and which are used to control the synchronous demodulator to rectify the AC signal output from the differential amplifier U3, the synchronous demodulator thereby acting as a phase sensitive full wave rectifier for the sinusoidal AC output of U3.

The sensor 50, and so the Wheatstone bridge, has both a resistive and a capacitive component to the moisture driven or moisture dependent differential output variation. While resistive changes are used for the present detailed description, it is recognized that the sensing and control system of the invention can be designed to operate based on either resistive or capacitive changes in the sensor signal. These signals are 90° out of phase as they are produced by the Wheatstone bridge, so that if the synchronous demodulator system, as timed by the output of U6, is in phase with the resistive component of the sensor output, for example, this is fully rectified and amplified as it leaves U5 as a DC signal. Because the capacitive component is 90° out of phase with the resistive component, it is nulled out. In this manner, the signal processing system amplifies the resistance related signal component only to modulate the signal on line 66 in a manner which eliminates the influence of the capacitive component. Of course, if desired and as mentioned above, the synchronization of the demodulation system can be shifted in phase to amplify instead the capacitive-related signal component.

The output of U5 on line 66 then is a DC signal proportional to the deviation of the bridge output from a setpoint based on changes in resistance only. That signal is fed to an integrator U2 and thereafter an amplifier U7 set at the proper gain to produce an output signal suitable to drive the heater at the desired level to heat the sensor and return the signal to a null. This modulation of power to the heater (designated A) adjusts the heater output to a level that will just compensate and return the conductivity of the sensor (LiCl) to its zero or setpoint and in so doing bring the Wheatstone bridge back to balance or null. The temperature sensing function integral with the sensor is schematically represented by B and B'.

Figure 4:
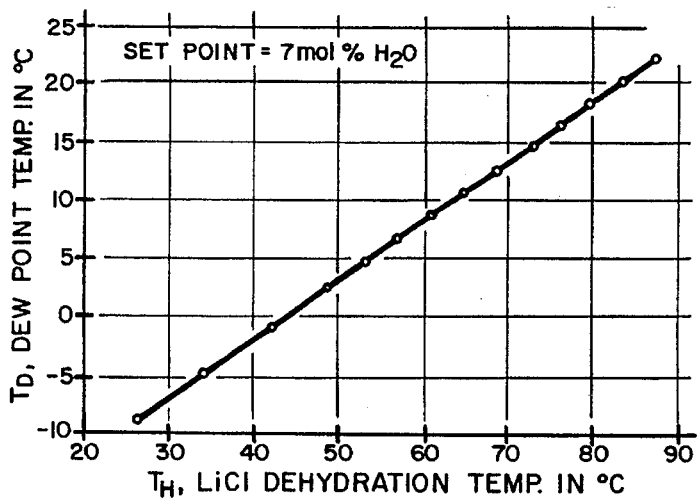
FIG. 4 is a graphical representation of the relation between dew point and the measured LiCl dehydration temperature.

FIG. 4 presents measured data that characterizes the linear relationship between the temperature of nulled resistance in the system or $T_H$ defined as the LiCl dehydration temperature and $T_D$ or the corresponding dew point. The set point chosen was 7 mol % $H_2O$ which is convenient for the range of ambient dew points indicated. In this manner, as long as the resistance or other chosen electrical parameter is constant (nulled), the salt temperature is directly indicative of the dew point. Knowledge of the ambient temperature as well enables RH data also to be directly available. While the relation depicted in FIG. 4 is considered relatively stable, over extended time sensor drift may introduce a degree of inaccuracy. As stated above, however, the use of a ratio of values based on different impressed frequencies as the control value eliminates this effect. The relation between the $T_D$ and $T_H$ is linear within a very small margin of error over a range of ambient temperatures up to 90° C.

Figure 5:
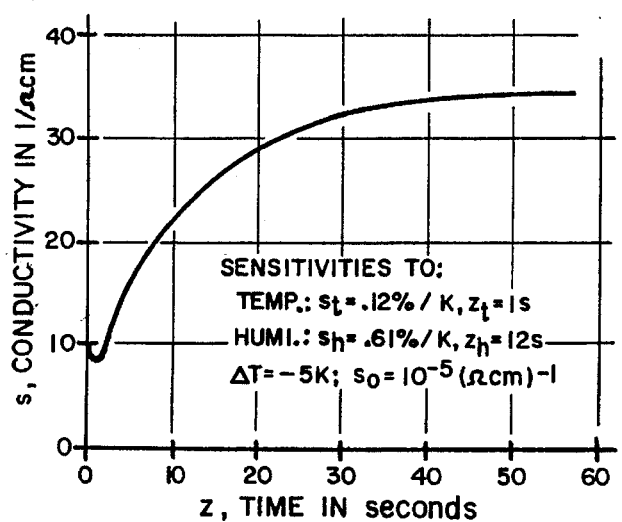
FIG. 5 is a graphical representation of the simulated response time, the electroconductivity of a LiCl dew point microsensor to a stepped change in temperature (ΔT)

FIG. 5 illustrates the change in conductivity of a LiCl salt bridge connecting sensor electrodes in accordance with the invention. The significance of the Figure is that it reveals the initial drop in conductance (0.0–0.2 sec) associated with a step change temperature reduction of 5K prior to the rapid increase (lasting about 25 sec) prior to stabilization of the conductivity value.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

We claim:

1. A sensor for determining the absolute amount of water vapor in the ambient atmosphere comprising:

(a) a thin film suspended ceramic structure of silicon nitride;

(b) a substantially planar patterned thin film heater carried within said suspended ceramic structure and having an open central region;

(c) a pair of substantially planar patterned interdigital electrodes forming an electrode area carried by said suspended ceramic structure, said electrodes further being proximate said heater but on the surface of the suspended structure and having a pattern dimension contained within the pattern of said heater;

(d) a film of an hygroscopic salt stabilized in a crosslinked polymer matrix host material substantially insoluble in an humidity-induced solution of said salt and connecting said pair of patterned electrodes; and (e) a patterned temperature sensing means for sensing the temperature of said salt, said temperature sensing means replacing said open central region of said heater.

2. The device of claim 1 wherein the electrodes are Au/Ag alloy.

3. The device of claim 1 wherein the hygroscopic salt is LiCl and the crosslinked polymer matrix is polyvinyl alcohol (PVA) crosslinked using dicarboxylic malonic acid.

4. The device of claim 1 wherein said temperature sensing means itself comprises a heating device replacing the central portion of the pattern of said heater to also provide temperature uniformity to said electrode area.

5. The device of claim 4 wherein said temperature sensor is of an interdigital pattern.

6. The sensor of claim 1 wherein the suspended structure is less than 2×2 mm in area.

7. The method of measuring relative humidity using exposed LiCl stabilized in a matrix of PVA crosslinked with malonic acid, temperature stabilized to a known value of an electrical characteristic thereof in which the stabilization temperature is indicative of the dew point and the ambient temperature with the dew point is representative of the relative humidity.

8. The device of claim 2 including means for sensing the temperature of the supporting ceramic structure as indicative of the atmosphere proximate said suspended ceramic structure.

9. A sensor for determining the absolute amount of water vapor in the ambient atmosphere comprising:

(a) a thin film suspended ceramic structure of silicon nitride;

(b) a substantially planar patterned thin film heater carried within said suspended ceramic structure;

(c) a pair of substantially planar patterned interdigital electrodes forming an electrode area carried by said suspended ceramic structure, said electrodes further being proximate said heater but on the surface of the suspended structure and having a pattern dimension contained within the pattern of said heater;

(d) a film of an hygroscopic salt stabilized in a crosslinked polymer matrix host material substantially insoluble in an humidity-induced solution of said salt and connecting said pair of patterned electrodes; and (e) a patterned temperature sensing means for sensing the temperature of said salt superimposed over the central region of said heater.

10. The method of depositing a film of metal alloy on a substrate from a plurality of targets of pure metals sought to be alloyed using a sputtering method which involves sequentially addressing the plurality of targets comprising the steps of:

(a) passing the substrate sequentially proximate to each of the plurality of targets for a plurality of cycles;

(b) depositing metal at each passage of the substrate proximate to a target, during the plurality of cycles to form a composite metal layer; and (c) optionally annealing the composite metal layer to achieve a uniform concentration of the plurality of metals in the composite metal layer.

11. The method of claim 10 wherein the pure metals are Au and Ag.

12. The method of claim 11 wherein step (c) comprises heating the layered substrate to approximately 450° C. in a forming gas comprising nitrogen and hydrogen.

13. The method of claim 11 further comprising the step of patterning the alloy on the substrate.

14. The method of claim 11 wherein the metal alloy is approximately Au 75% and Ag 25%.

15. The method of measuring dew point using exposed LiCl, stabilized in a matrix of PVA crosslinked with malonic acid, temperature stabilized to a known value of an electrical characteristic thereof in which the stabilization temperature is indicative of the dew point.

16. A method of humidity stabilizing an hygroscopic salt exposed to the atmosphere under conditions of high humidity comprising the step of retaining said hygroscopic salt in an host material, said host material comprising a polymer matrix, said polymer matrix being substantially insoluble in an humidity induced water solution of the hygroscopic salt, said polymer matrix further comprising a hydrophilic polymer crosslinked using a cross-linking agent wherein said hydrophilic polymer comprises cross-linked polyvinyl alcohol (PVA) and the crosslinking agent comprises a malonic acid.

17. The method of claim 16 wherein the hygroscopic salt comprises LiCl.

18. The method of claim 17 wherein the ratio of PVA to LiCl is from about 2:1 to about 1:2.

19. The method of claim 18 wherein the ratio of PVA to malonic acid is from about 1:(0.12) to about 1:(0.36).

20. A stabilized hygroscopic alkali halide salt composite material having a retention property in a host medium that provides for use involving repeated exposure to high humidity as in a dew point or absolute water vapor sensor comprising an amount of alkali halide salt stabilized in a host material selected from polymer matrices of a poly alcohol crosslinked using a carboxylic agent wherein the host material is a polymer matrix in which the poly alcohol is polyvinyl alcohol (PVA) and the carboxylic acid is malonic acid.

21. The composite of claim 20 wherein the hygroscopic salt is LiCl.

22. The composite of claim 21 wherein the ratio of PVA to LiCl is from about 2:1 to about 1:2.

23. The composite of claim 22 wherein the ratio of PVA to malonic acid is from about 1:(0.12) to 1:(0.36).

24. A device for determining the dew point or absolute atmosphere water vapor content comprising:

(a) an hygroscopic salt exposed to exchange water vapor with the atmosphere but stabilized against washout in a retaining host material selected from the group consisting of porous alumina, magnesia, zirconia, silicon film and polymer matrices selected from those comprising crosslinked hydrophilic polymers substantially insoluble in a humidity induced solution of the hygroscopic salt;

(b) heating means proximate said hygroscopic salt for controlling the temperature of said salt to maintain a selected electrical parameter of said salt at a predetermined value independent variations in conditions of the atmosphere, wherein said parameter is selected from the group consisting of the electrical impedance components, resistance, and capacitance;

(c) means for measuring said selected electrical parameter of said salt;

(d) means for measuring the temperature of said salt and optionally of said atmosphere; and (e) wherein the host material is a polymer matrix comprising polyvinyl alcohol crosslinked using malonic acid.

25. The device of claim 24 wherein the hygroscopic salt is LiCl.

26. A device for determining the dew point or absolute atmosphere water vapor content comprising:

(a) an hygroscopic salt exposed to exchange water vapor with the atmosphere but stabilized against washout in a retaining host material selected from the group consisting of porous alumina, magnesia, zirconia, silicon film and polymer matrices selected from those comprising crosslinked hydrophilic polymers substantially insoluble in a humidity induced solution of the hygroscopic salt;

(b) heating means proximate said hygroscopic salt for controlling the temperature of said salt to maintain a selected electrical parameter of said salt at a predetermined value independent variations in conditions of the atmosphere, wherein said parameter is selected from the group consisting of the electrical impedance components, resistance and capacitance;

(c) means for measuring said selected electrical parader of said salt;

(d) means for measuring the temperature of said salt and optionally of said atmosphere; and (e) means for applying an AC signal at a plurality of frequencies to said sensor and means for measuring the selected electric parameter at two different frequencies to produce a ratio thereof.

27. The device of claim 26 wherein the electrical parameter is resistance.

28. The device of claim 26 wherein the electrical parameter is capacitance.

29. A device for determining the absolute amount or water vapor in the atmosphere comprising:

(a) a thin film suspended ceramic structure;

(b) an hygroscopic salt exposed to the atmosphere but retained in a polymeric matrix host material substantially insoluble in an humidity-induced solution of said salt carried on said suspended ceramic structure;

(c) thin film heating means carried on said suspended ceramic structure proximate said hygroscopic salt for controlling the temperature thereof to maintain a selected electrical parameter of said salt at a predetermined value independent of variations in conditions of the atmosphere, wherein said parameter is selected from the group of impedance components consisting of electric resistance and capacitance;

(d) means for measuring said selected electrical parameter of said salt;

(e) means for measuring the temperature of said salt and optionally of said atmosphere; and (f) wherein the polymeric matrix is a malonic acid crosslinked polyvinyl alcohol and the hygroscopic salt is LiCl.

30. A device for determining the absolute amount or water vapor in the atmosphere comprising:

(a) a thin film suspended ceramic structure;

(b) an hygroscopic salt exposed to the atmosphere but retained in a polymeric matrix host material substantially insoluble in an humidity-induced solution of said salt carried on said suspended ceramic structure;

(c) thin film heating means carried on said suspended ceramic structure proximate said hygroscopic salt for controlling the temperature thereof to maintain a selected electrical parameter of said salt at a predetermined value independent of variations in conditions of the atmosphere, wherein said para mer is selected from the group of impedance components consisting of electric resistance and capacitance;

(d) means for measuring said selected electrical parameter of said salt;

(e) means for measuring the temperature of said salt and optionally of said atmosphere; and (f) means for applying an AC signal at a plurality of frequencies to said sensor and means for measuring the selected electric parameter at two different frequencies to produce a ratio thereof.

31. The device of claim 30 wherein the impedance component selected is resistance.

32. The device of claim 30 wherein the impedance component selected is capacitance.

33. The device of claim 30 wherein the thin, film suspended ceramic structure is silicon nitride.

34. A method of humidity stabilizing an hygroscopic salt exposed to the atmosphere under conditions of high humidity comprising the step of retaining said hygroscopic salt as a separated incorporated salt in an host material selected from the group consisting of porous alumina, magnesia, zirconia, silicon films and hydrophilic polymer matrices which are substantially insoluble in an humidity induced water solution of the hygroscopic salt, said polymer matrices further being selected from a poly alcohol crosslinked by a carboxylic crosslinking agent; thereby yielding a host material which resists washout of said hygroscopic salt.

35. The method of claim 34 wherein the hygroscopic salt comprises LiCl.

36. A stabilized hygroscopic alkali halide salt composite material having a retention property in a host medium that provides stabilization against washout of alkali halide salt and provides capability for use involving repeated exposure to high humidity as in a dew point or absolute water vapor sensor comprising an amount of alkali halide salt stabilized as a separately incorporated salt in a host material selected from the group consisting of porous alumina, magnesia, zirconia, silicon film and a polymer hydrophilic matrix of a poly alcohol crosslinked using an acid crosslinking carboxylic agent.

37. A device for determining the absolute amount of water vapor in the atmosphere surrounding said device comprising:

(a) a thin film suspended ceramic structure;

(b) an hygroscopic salt exposed to the atmosphere but retained in a hydrophilic polymeric matrix host material as a separately incorporate salt substantially insoluble in an humidity-induced solution of said salt carried on said suspended ceramic structure;

(c) thin film heating means carried on said suspended ceramic structure proximate said hygroscopic salt for controlling the temperature thereof to maintain a selected electrical parameter of said salt at a predetermined value independent of variations in conditions of the atmosphere, wherein said parameter is selected from the group of impedance components consisting of electric resistance and capacitance;

(d) means for measuring said selected electrical parameter of said salt; and (e) means for measuring the temperature of said salt and optionally of said atmosphere.

* * * * *